United States Patent [19]

Sperinde

[11] Patent Number: 4,623,248
[45] Date of Patent: Nov. 18, 1986

[54] APPARATUS AND METHOD FOR DETERMINING OXYGEN SATURATION LEVELS WITH INCREASED ACCURACY

[75] Inventor: John M. Sperinde, San Jose, Calif.

[73] Assignee: Abbott Laboratories, North Chicago, Ill.

[21] Appl. No.: 467,087

[22] Filed: Feb. 16, 1983

[51] Int. Cl.$^4$ .................... G01N 33/48; G01N 33/72
[52] U.S. Cl. ..................................... 356/41; 128/634
[58] Field of Search ............................. 356/39, 40, 41; 128/633, 634

[56] References Cited

U.S. PATENT DOCUMENTS 3,847,483 11/1974 Shaw et al. ........................ 356/41
4,114,604 9/1978 Shaw et al. ........................ 356/41

Primary Examiner—Vincent P. McGraw
Attorney, Agent, or Firm—Robert W. Stevenson; Martin L. Katz; Robert S. Kelly

[57] ABSTRACT

A catheter oximeter includes a fiber optic catheter for supplying radiation to blood under test at a plurality of wavelengths and detecting the intensities of the radiation back-scattered from the blood at each of the wavelengths. The oxygen saturation level of the blood is then computed by deriving it with a formula which uses the ratio of one pair of intensity signals when the oxygen saturation level is relatively low and with a formula which uses the ratio of another pair of intensity signals when the oxygen saturation level relatively is high.

7 Claims, 6 Drawing Figures

APPARATUS AND METHOD FOR DETERMINING OXYGEN SATURATION LEVELS WITH INCREASED ACCURACY

TECHNICAL FIELD

The present invention relates to catheter oximeters in general and more particularly concerns an apparatus and method for computing oxygen saturation levels of blood under test wherein the detected intensities of radiation back-scattered from the blood are manipulated to provide a value indicative of blood oxygen saturation level.

BACKGROUND ART

The viability of every cell in the human body depends upon an adequate supply of oxygen. Paradoxically, despite its role as the body's most important metabolite, oxygen is not stored in significant quantities by the body. Continuous and adequate transport of oxygen to the body cells is instead normally established by directing a constant flow of blood-laden oxygen from the lungs through the body's blood circulatory system to the individual body cells in need of oxygen. Interruption in the oxygen transport process for even brief periods of time can result in unconsciousness and death. Unfortunately, many otherwise salutary clinical or surgical procedures present the risk of such interruption, and the desirability of undertaking these clinical or surgical proceedings is dependent upon the ability of the attending surgical staff to obtain accurate, continuous real-time measurements of oxygen levels in the blood. If blood oxygen levels thus monitored drop dangerously, appropriate emergency procedures can be undertaken to protect the life of the patient.

One of the more practical methods for ascertaining the amount of oxygen in the blood involves determining the blood oxygen saturation level. The oxygen saturation level is a measure of the amount of oxygenated hemoglobin present in the bloodstream relative to all of the hemoglobin present in the bloodstream. Hemoglobin in turn is a conjugated protein which is present in red blood cells. Practically speaking, red blood cells are formed as bioconcave discs of approximately 10 micrometers diameter and commonly exist in densities of approximately five million red blood cells per cubic millimeter. It is known that red blood cells both scatter and transmit radiant energy incident thereon in amounts which vary as a function of the oxygen content of the hemoglobin in the cells. The differential absorption of radiant energy between oxygenated and non-oxygenated hemoglobin as radiant energy is transmitted through red blood cells furnishes a convenient basis for measuring oxygen saturation levels.

Oxygen saturation level measurements can be performed by utilizing an indwelling intravascular catheter which conducts radiant energy from an external light source to an in vivo measurement site and returns energy reflected or scattered back from the red blood cells to an external detector. Intravascular catheters of this type, known as optical catheters, generally include transmitting and receiving fiber optic light guides for respectively conducting radiant energy to and returning radiant energy from the in vivo measurement site. The transmitting fiber optic light guide has an inlet aperture connected to an LED or other light source while the receiving fiber optic light guide has an outlet aperture connected to a photodetector. The outlet aperture of the transmitting fiber optic light guide is commonly oriented in a co-planar relationship with the inlet aperture of the receiving fiber optic light guide. Radiant energy admitted to the in vivo measurement site through the outlet aperture of the transmitting fiberoptic light guide is both absorbed and back-scattered by the red blood cells in the vicinity of the in vivo measurement site, with the amount of absorption varying as a function of the oxygen content of the blood cell hemoglobin as described above. A portion of the radiation back-scattered from the blood, hereinafter simply referred to as "back-scattered radiation," enters the inlet aperture of the receiving fiber optic light guide and is driected to the photodetector where the intensity of the back-scattered radiation can be ascertained. Due to the variation in radiation absorption brought about by changes in the oxygen saturation level of the blood under test, the total amount of back-scattered radiation available for detection at the photodetector likewise varies as a function of oxygen saturation. The oxygen saturation level may thus be computed using the detected intensities of the radiation returned from the in vivo measurement site. One prior art equation employed for oxygen saturation level computations based on radiation intensity determinations is of the form:

$$S_3 = A_0 + A_1(I_3/I_2) = A_0 + A_1 R_3 \quad (1)$$

where $I_2$ represents the intensity of back-scattered radiation returned from the blood at wavelength $\lambda_2$, $I_3$ represents the intensity of back-scattered radiation returned at wavelength $\lambda_3$. $R_3$ is the ratio between $I_3$ and $I_2$ and $A_0$ and $A_1$ are empirically derived calibration coefficients. In the two-wavelength measuring system necessary to implement Equation (1), $\lambda_3$ is usually an isosbestic wavelength, i.e., a wavelength at which little or no difference appears in the optical absorptance of oxygenated hemoglobin versus non-oxygenated hemoglobin, while $\lambda_2$ is a non-isosbestic wavelength.

Inasmuch as the amount of radiation actually back-scattered from red blood cells at the in vivo measurement site represents a very small fraction of the total radiation transmitted to the in vivo measurement site, the intensity of back-scattered radiation received at the inlet aperture to the receiving fiber optic light guide is greatly influenced by many factors in addition to the differential absorption qualities of the oxygenated and non-oxygenated hemoglobin. For example, changes in the number of red blood cells, their location, size, shape and orientation can all affect the extent to which back-scattering occurs. Moreover, the blood under test flows past the in vivo measurement site in a pulsatile fashion, causing the tip of the optical catheter to move in an uncontrolled manner with respect to the blood vessel walls. Whenever a blood vessel wall appears in the near field of the catheter tip, a very large array of tightly-packed back-scattering blood cells is introduced into the measurement system. This cell packing phenomenon results in a significant variation in the distribution and number of back-scattering blood cells, producing substantial and wavelength-dependent changes in the intensities of radiation returned to the receiving fiber optic light guide. Wavelength-dependent radiation intensity fluctuations, of course, affect the overall accuracy of oxygen saturation level computations obtained from radiation-dependent equations such as Equation (1).

In order to compensate for inaccuracies in Equation (1) attributable to uncontrollable changes in the aforementioned physiologic parameters, new equations have been developed. For example, U.S. Pat. No. 3,847,483 issued to Shaw, et al., proposes a two-wavelength measuring system in which oxygen saturation levels can be determined according to the relationship:

$$S_2 = \frac{B_0 + B_2 I_1 + B_2 I_2}{C_0 + C_1 I_1 + C_2 I_2} \quad (2)$$

where $I_1$ and $I_2$ are the back-scattered radiation intensities detected at wavelengths $\lambda_1$ and $\lambda_2$ respectively and $B_0$, $B_1$, $B_2$, $C_0$, $C_1$ and $C_2$ are empirically derived calibration or weighting coefficients. Neither $\lambda_1$ and $\lambda_2$ need be isosbestic wavelengths. Dividing both the numerator and denominator of Equation (2) by $1/I_1$ yields:

$$S_2 = \frac{B_0/I_1 + B_1 + B_2(I_2/I_1)}{C_0/I_1 + C_1 + C_2(I_2/I_1)} = \frac{B_0/I_1 + B_1 + B_2 R_2}{C_0/I_1 + C_1 + C_1 R_2} \quad (3)$$

where $R_2$ is the ratio between $I_2$ and $I_1$. As can be seen, Equation (3) attempts to offset errors in oxygen saturation level calculations by utilizing intensity ratios to minimize the effect of fluctuations in the intensity measurements. However, as noted in U.S. Pat. No. 4,114,604 issued to Shaw, et al., oxygen saturation level measurements determined in accordance with Equation (3) to some extent remain a function of individual light intensities as well as the aforementioned physiologic phenomena such as blood flow velocity, hematocrit, pH and pCO$_2$. As a more accurate alternative to Equations (1) and (2), U.S. Pat. No. 4,114,604 offers yet another equation, i.e.:

$$S_{1,3} = \frac{B_0 + B_1(I_1/I_2) + B_2(I_1/I_2)^2 + B_3(I_3/I_2)}{C_0 + C_1(I_1/I_2) + C_2(I_1/I_2)^2 + C_3(I_3/I_2)} \quad (4)$$

where $I_1$, $I_2$ and $I_3$ are intensities of back-scattered radiation respectively detected at wavelengths $\lambda_1$, $\lambda_2$ and $\lambda_3$ and normalized against a reference light intensity, $B_0$, $B_1$, $B_2$ and $B_3$ are weighting factors or coefficients and $C_0$, $C_1$, $C_2$ and $C_3$ are likewise weighting factors or coefficients. Substituting $R_1$ for the ratio $I_1/I_2$ and $R_3$ for the ratio $I_3/I_2$ yields:

$$S_{1,3} = \frac{B_0 + B_1 R_1 + B_2 R_1^2 + B_3 R_3}{C_0 + C_1 R_1 + C_2 R_1^2 + C_3 R_3} \quad (5)$$

In operation, the apparatus disclosed in U.S. Pat. No. 4,114,604 for implementing Equation (5) is a three-wavelength oximeter which transmits radiation to the in vivo measurement site at wavelengths of approximately 670 nanometers, 700 nanometers and 800 nanometers. These wavelengths were empirically selected on the basis of data taken from a large number of in vitro studies conducted on anesthetized experimental animals, human volunteers and clinical patients undergoing surgery and intensive care. For each of the wavelengths selected, the ratio of back-scattered intensities as a function of actual oxygen saturation level has been plotted, using the physiologic parameter of hematocrit as a variable. This plot is reproduced in FIG. 1, with $R_1$ representing the ratio of back-scattered intensities at 670 nm and 700 nm and $R_3$ representing the ratio of back-scattered intensities at 800 nm and 700 nm. Each of the ratios $R_1$ and $R_3$ has been observed and plotted at respective hematocrit values of 0.25 and 0.45. The latter values are respectively near the lower and upper extremes of the range of hematocrit values of interest. From the graph of FIG. 1, it can be seen that $R_3$ is relatively independent of changes in hematocrit value at oxygen saturation levels of approximately 36% but varies greatly with changes in hematocrit value throughout the upper regions, i.e., the 60%–90% regions, of the oxygen saturation level range. On the other hand, $R_1$ is relatively independent of changes in hematocrit value at oxygen saturation levels of approximately 90% but varies widely with changes in the hematocrit value throughout the lower regions of interest in the oxygen saturation level range. Similar behavior of $R_1$ and $R_3$ has been observed with respect to changes in blood pH, blood pCO$_2$ and like parameters.

Upon reflection, it should be evident that error in the computed oxygen saturation level resulting from changes in physiologic parameters can be minimized by weighting Equation (5) in favor of that ratio of back-scattered radiation which exhibits minimum variation as a function of the given physiologic parameter in the oxygen saturation range of interest. Conversely, Equation (5) should be weighted most heavily against that ratio of back-scattered radiation which exhibits maximum variation as a function of the given physiologic parameter in the oxygen saturation range of interest. If the aforementioned weighting is performed, the value obtained from Equation (5) for any given set of detected back-scattered radiation ratios will depend primarily on the most stable ratio in the set. Actual selection of proper factors or coefficients in Equation (5) can be carried out empirically by substituting coefficient values until the differential of computed oxygen saturation level with respect to each ratio of back-scattered radiation approximates zero at a point where the remaining ratio of back-scattered radiation experiences the least variation in response to change in the physiologic parameter.

It will be recalled from FIG. 1 that the ratio $R_3$ varies minimally while the ratio of $R_1$ varies greatly in response to changes in hematocrit at oxygen saturation levels ranging between 25% and 45%. In contrast, the variation of $R_1$ as a function of hematocrit is minimal while that of $R_3$ is large at oxygen saturation levels ranging between 85% and 100%. Errors introduced into the computation of oxygen saturation level as a result of changes in the unmeasured hematocrit will thus be significantly reduced if Equation (5) is made to depend most heavily upon $R_3$ in the range of 25% to 45% OS and on $R_1$ in the range of 85% to 100% OS. The required conditions can be established by selecting the Equation (5) weighting factors such that the derivative of Equation (5) with respect to $R_1$ approximates zero in the range of 25% to 45% OS, i.e.:

$$\frac{\partial S_{1,3}}{\partial R_1} \simeq 0 \text{ at } 25\% \leq OS \leq 45\% \quad (6)$$

The derivative of Equation (5) with respect to $R_3$ should approximate zero in the range of 85% to 100% OS, i.e., $$\frac{\partial S_{1,3}}{\partial R_3} \simeq 0 \text{ at } 85\% \leq OS \leq 100\% \tag{7}$$

When the latter constraints are simultaneously satisfied, as illustrated in FIG. 2, errors in computations of oxygen saturation levels based on measurements of intensity ratios will tend to be minimized in relation to changes of non-measured but wavelength-dependent blood characteristics other than oxygen saturation level.

Although use of Equation (5) together with appropriate weighting coefficients improves the accuracy of oxygen saturation level computations, additional empirical data has revealed that the aforementioend weighting constraints as applied to Equation (5) cannot be completely satisfied. In particular, the relationship expressed in Equation (6) is easier to achieve than that expressed in Equation (7) and hence the empirically determined coefficients tend to weight $R_1$ more heavily than $R_3$. Inasmuch as variations in $R_1$ brought about by changes in the non-measured hematocrit tend to decrease as the oxygen saturation level increases, the weighting bias in favor of $R_1$ will enhance the accuracy of Equation (5) at the high end of the oxygen saturation range. At lower levels of oxygen saturation, variation in the value of $R_1$ due to changes in unmeasured hematocrit increase and the inability to completely satisfy Equation (7) leaves Equation (5) more vulnerable to error introduced by unaccountable shifts in $R_1$.

DISCLOSURE OF THE INVENTION

It is therefore an object of the present invention to construct a catheter oximeter which operates to provide accurate computations of oxygen saturation in blood under test at both the high and low ends of the oxygen saturation level range.

It is another object of the present invention to provide a catheter oximeter which detects intensities of radiation back-scattered from blood under test and which thereafter employs the values of the detected intensities to compute the blood oxygen saturation level using one of two equations selected to minimize the influence of unmeasured blood parameters on the final oxygen saturation level computations.

These and other objects of the present invention are achieved in a catheter oximeter which generates radiation at three distinct wavelengths and directs the radiation so generated to blood at a measurement site. The radiation is absorbed and back-scattered by the blood at the measurement site and a portion of the back-scattered radiation is returned to the oximeter for detection of the back-scattered radiation intensity. Ratios of the detected intensities are then derived and employed in Equations (5) and (1) above to obtain values for $S_{1,3}$ and $S_3$. If the oximeter is operating in the arterial mode, i.e., if the blood under test is flowing through an arterial vessel, the $S_{1,3}$ value obtained from Equation (5) is used to provide an indication of oxygen saturation level unless it appears that the oxygen saturation level is less than 40% OS. In the latter case, the $S_3$ value obtained from Equation (1) is retained as the final indication of oxygen saturation level. When the oximeter is operating in the venous mode, i.e., when the blood under test is flowing through a venous vessel, Equation (1) serves as a baseline for establishing a deviation value D. D is both added to and subtracted from $S_3$ to define an "error envelope" above oxygen saturation levels of 60%. Where the $S_3$ value obtained from Equation (1) is less than 60% OS, $S_3$ again provides the final indication of oxygen saturation level. Where, however, $S_3$ is greater than 60% OS, Equation (5) is employed as the primary equation for determining oxygen saturation level unless the $S_{1,3}$ value obtained from Equation (5) falls outside the "error envelope" defined by $S_3 \pm D$.

BRIEF DESCRIPTION OF THE DRAWINGS

The various objects, features and advantages of the present invention will be better understood by considering the following Brief Description of the Drawings and Best Mode for Carrying Out the Invention, in which.

BEST MODE FOR CARRYING OUT THE INVENTION

Figure 3:
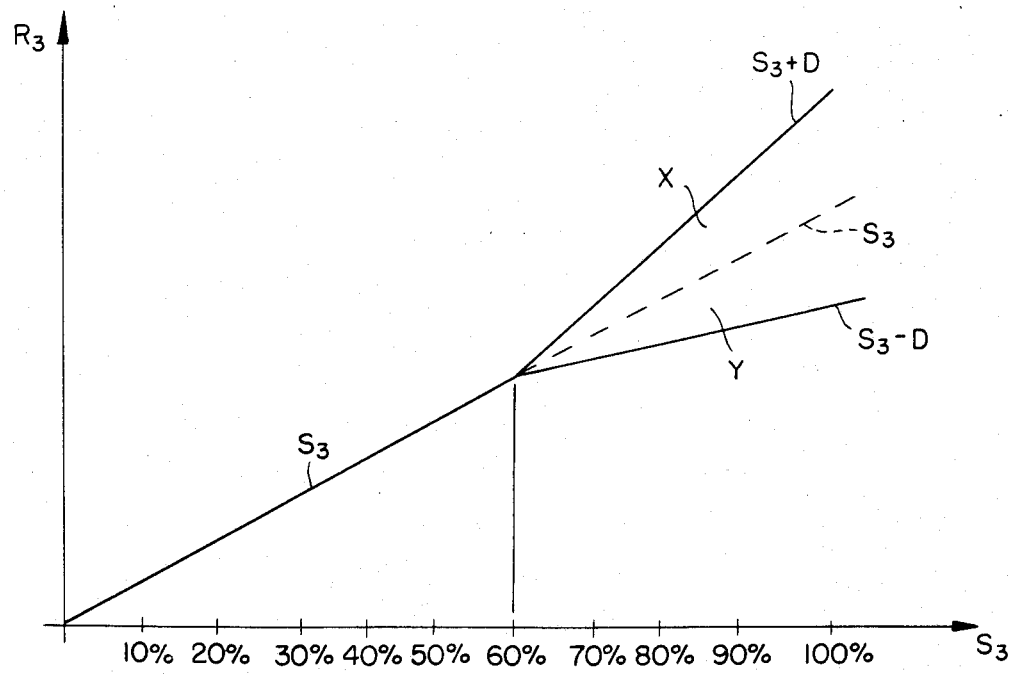
FIG. 3 is a graph of $S_3$ versus $R_3$, showing the "error envelope" defined in accordance with the present invention.

Due to the fact that empirically derived weighting coefficients bias Equation (5) in favor of $R_1$ as discussed in the Background Art Section above, use of Equation (5) to compute oxygen saturation levels will yield most accurate results when measurements of back-scattered radiation intensities are performed in oxygen-rich environments. More particularly, the accuracy of Equation (5) will be least affected during in vivo determinations of oxygen saturation in blood flowing through arterial vessels, where oxygen saturation levels are typically high. When performing oxygen saturation computations based on $R_1$ and $R_3$ measurements taken from venous blood, where oxygen saturation levels are reduced, the accuracy of Equation (5) is diminished as also discussed above and some means must be found to compensate for the tendency of Equation (5) to weight $R_1$ more heavily. Such compensation can be obtained in the venous measurement mode by establishing an "error envelope" for oxygen saturation level computations based on reasonable assumptions about the behavior of Equation (5) at lower oxygen saturation levels. If oxygen saturation level computations fall within this "error envelope," the computations are taken as valid and are treated accordingly. Computations falling outside the "error envelope" are discarded. FIG. 3 illustrates the error envelope principle. In FIG. 3, oxygen saturation level computations obtained from Equation (1) are plotted against measured $R_3$ intensity ratios to furnish a baseline against which the "error envelope" can be drawn. Equation (1) is chosen as the baseline because it is dependent solely upon $R_3$ and therefore supplies accurate values for oxygen saturation at lower oxygen saturation levels. Indeed, because of the biasing in favor of $R_1$ exhibited by Equation (5), Equation (1) is the most accurate of the two equations at oxygen saturation levels below approximately 60%. At oxygen saturation levels of 60% or above, a deviation value D which progressively increases as the value of Equation (1) increases is used to define the "error envelope." Specifically:

$$D = 0.1 \times (S_3 - 0.6) \quad (8)$$

where $S_3$ is the value of the oxygen saturation level obtained from Equation (1). The deviation value D is both added to and subtracted from the value of $S_3$, creating a triangular area in FIG. 3 bounded on one side by an $S_3 + D$ curve and on the other side by an $S_3 - D$ curve. This triangular area, which has a base width of 2D, provides the "error envelope" for evaluating the accuracy of the oxygen saturation level computation obtained from Equation (5). Equation (5) is employed for oxygen saturation level computations only where the value derived from Equation (5) falls within the "error envelope." Consequently, a decision must be made as to whether $S_{1,3}$ is greater or less than the boundary curves of the "error envelope." The decisional scheme to accomplish this end may be implemented as follows. First, the values of $S_3$ and $S_{1,3}$ are calculated using the detected intensities of back-scattered radiation at the $\lambda_1$, $\lambda_2$ and $\lambda_3$ wavelengths to derive corresponding values for $R_1$ and $R_3$. The empirically determined values for $A_0$, $A_1$, $B_0$-$B_3$ and $C_0$-$C_3$ are then combined with the values of $R_1$ and $R_3$ in Equations (1) and (5) to obtain $S_3$ and $S_{1,3}$. 60% OS is next set as a cutoff point against which $S_3$ is compared. If $S_3$ is greater than 60% OS, i.e., if:

$$S_3 > 0.6 \quad (9)$$

the value of $S_{1,3}$ is compared to the value of $S_3$ to ascertain whether $S_{1,3}$ is greater or less than $S_3$. When $S_{1,3}$ is greater than $S_3$, the value of $S_{1,3}$ is retained as the oxygen saturation level computation $SO_2$ only if the value of $S_{1,3}$ falls within the area X of the "error envelope" bounded by the $S_3 + D$ curve. That is, when:

$$S_{1,3} > S_3 \quad (10)$$

$$SO_2 = \text{Min}(S_{1,3}, S_3 + D) \quad (11)$$

When $S_{1,3}$ is less than $S_3$, the value of $S_{1,3}$ is retained as the oxygen saturation level computation $SO_2$ if $S_{1,3}$ falls within the area Y bounded by the $S_3 - D$ curve. That is, when:

$$S_{1,3} < S_3 \quad (12)$$

$$SO_2 = \text{Max}(S_{1,3}, S_3 - D) \quad (13)$$

As previously noted. Equation (1) is acceptably accurate at oxygen saturation levels below 60%. Hence, where:

$$S_3 > 0.6 \quad (14)$$

$$SO_2 = S_3 \quad (15)$$

Figure 4:
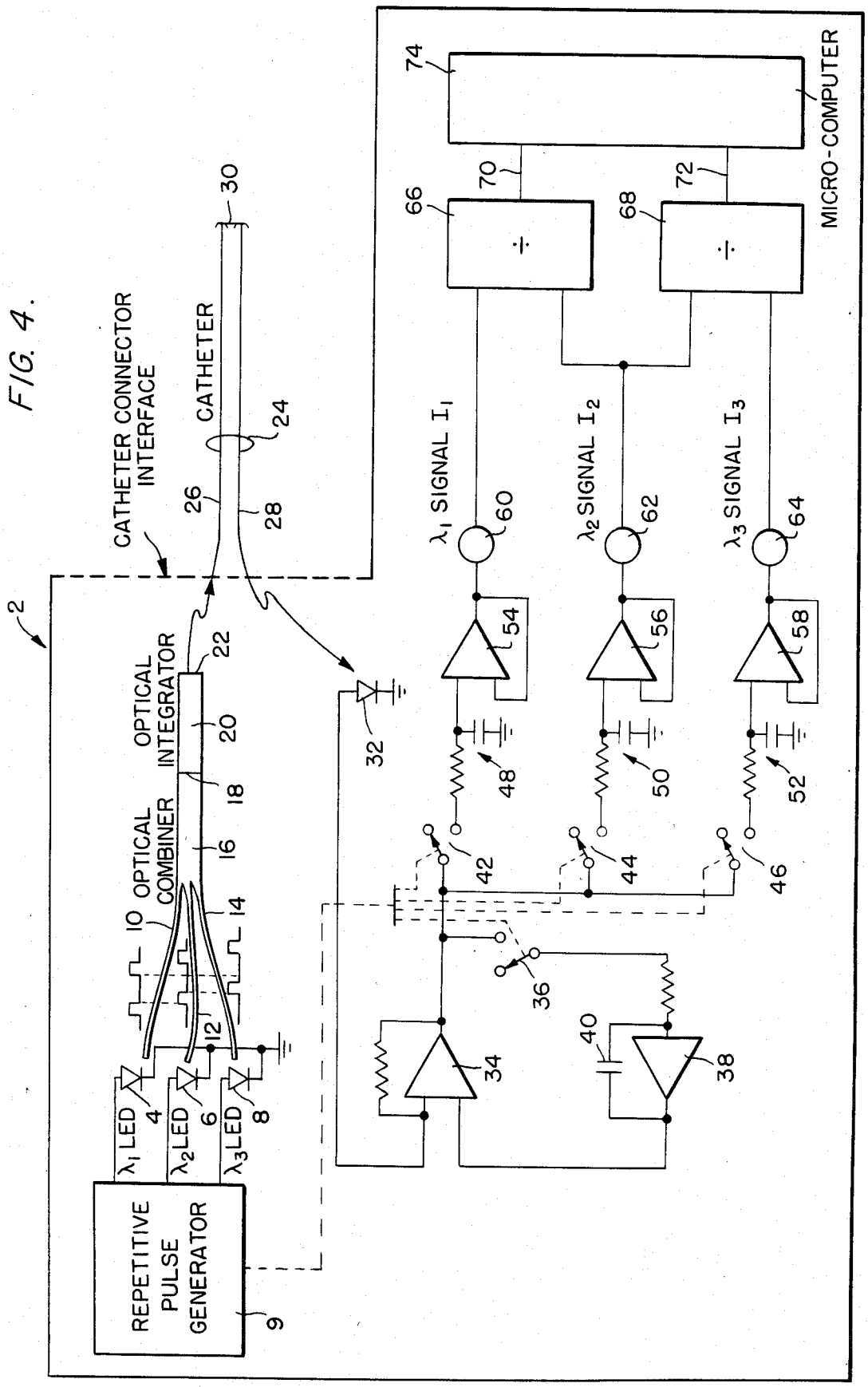
FIG. 4 is a circuit diagram of a catheter oximeter constructed in accordance with the present invention.

A catheter oximeter capable of performing the computations and decisions indicated in Equations (2), (5) and (8)–(15) can be seen in FIG. 4. The oximeter 2 comprises a radiation source, an optical combiner and integrator means, an optical detector and a signal processing means. The radiation source includes three light-emitting diodes 4, 6 and 8 which are arranged to emit radiation at wavelengths $\lambda_1$, $\lambda_2$ and $\lambda_3$, respectively. A pulse generator 9 sequentially energizes each of the light-emitting diodes 4–8 in non-overlapping temporal fashion to establish three separate periods of light emission, each of which periods is associated with a respective $\lambda_1$, $\lambda_2$ or $\lambda_3$ wavelength. The three periods of light emission are followed by a period in which none of the light-emitting diodes 4–8 is energized. One cycle of pulse generator operation thus contains four approximately equal periods, and 250 such cycles may occur per second.

The radiation from light-emitting diodes 4–8 is respectively collected by a series of fiber optic guides 10, 12 and 14. Each of the fiber optic guides 10–14 may contain one or more optical fibers which physically merge into a bundle to form an optical combiner 16 having an end surface 18. An optical integrator 20 abuts the end 18 of optical combiner 16. Optical integrator 20 is a single light guide having a square cross sectional area of approximately the same size as the cross-sectional area of end surface 18 on optical combiner 16. The optical integrator 20 assures that spatially-separated radiation reaching the optical integrator from end surface 18 of optical combiner 16 is uniformly distributed over the exit aperture 22 of the optical integrator. An optical catheter 24 receives the radiation leaving the exit aperture 22 of optical integrator 20. Optical catheter 24 includes a transmitting fiber optic guide 26 for transmitting radiation to the blood under test at each of the three wavelengths $\lambda_1$, $\lambda_2$ and $\lambda_3$ associated with the light-emitting diodes 4–8. Optical catheter 24 also includes a receiving fiber optic guide 28 which receives radiation back-scattered by the blood under test. Transmitting fiber optic guide 26 and receiving fiber optic guide 28 may both consist of only a single optical fiber, thereby greatly simplifying the construction of the optical catheter and making possible a low-cost disposable catheter configuration.

When the distal tip 30 of optical catheter 24 is immersed in a blood vessel or other blood-confining container, radiation at each of the three wavelengths $\lambda_1$, $\lambda_2$ and $\lambda_3$ is emitted from the distal aperture of the transmitting fiber optic guide and is selectively absorbed and back-scattered by the red blood cells. A portion of the back-scattered radiation at each of the three wavelengths enters the distal aperture of the receiving fiber optic guide and is returned to the catheter oximeter 2. The proximal aperture of the receiving fiber optic guide is optically coupled to a radiation detector 32, causing substantially all of the radiation exiting from the receiving fiber optic guide to impinge upon the active area of the radiation detector. The radiation detector outputs a series of signals respectively associated with each of the three wavelengths $\lambda_1$-$\lambda_3$, which signals are amplified by a detector amplifier 34. Compensation for drift in detector amplifier 34 and for spurious outputs from radiation detector 32 are achieved by driving the output voltage of the detector amplifier to zero in those intervals when no back-scattered radiation reaches the radiation detector. To this end, a switch 36 is closed by a signal from the pulse generator 9 to form a closed loop servo system between amplifier 34 and a second amplifier 38 during the one period of the pulse generator operating cycle when none of the light-emitting diodes 4–8 is emitting radiation. The closed loop servo system establishes a bias voltage on amplifier 34, adjusting its output voltage to zero. During the remaining three periods of each pulse generator operating cycle when light-emitting diodes 4-8 are sequentially emitting radiation, switch 36 is opened by a signal from the pulse generator but the bias voltage necessary for driving the output of amplifier 34 to zero in the absence of an incoming signal from radiation detector 32 is maintained by an operationally connected feedback capacitor 40.

The signal voltages generated at the output of the detector amplifier 34 in response to back-scattered radiation reaching radiation detector 32 are respectively supplied through three switches 42, 44 and 46 to three RC filter networks 48, 50 and 52. Switches 42-46 are controlled by pulse generator 9 in accordance with the sequential energization of light-emitting diodes 4-8. Consequently, switch 42 is closed when light-emitting diode 4 is emitting radiation at wavelength $\lambda_1$, switch 44 is closed when light-emitting diode 6 is emitting radiation at wavelength $\lambda_2$ and switch 46 is closed when light-emitting diode 8 is emitting radiation at wavelength $\lambda_3$. The action of RC network 48 produces an average signal voltage representative of the intensity of the radiation at the $\lambda_1$ wavelength back-scattered from the blood under test. This average signal voltage is amplified by amplifier 54 to provide a continous output voltage directly related to the intensity of radiation at the $\lambda_1$ wavelength back-scattered from the blood under test. Similarly, the action of RC network 50 and amplifier 56 combine to produce a continous output voltage directly related to the intensity of radiation at the $\lambda_2$ wavelength back-scattered from blood under test while the action of RC network 52 and amplifier 58 combine to produce a continuous output voltage directly related to the intensity of radiation at the $\lambda_3$ wavelength back-scattered from the blood under test. The output voltages from amplifiers 54-58 are directed to terminals 60, 62 and 64, whereupon a dividing circuit 66 connected to terminals 60 and 62 generates a signal having a magnitude corresponding to the ratio of $I_1/I_2$, i.e., corresponding to the ratio $R_1$. A similar dividing circuit 68 connected to terminals 62 and 64 generates a signal having a magnitude corresponding to the ratio of $I_3/I_2$, i.e., corresponding to the ratio $R_3$. The signals from dividing circuits 66 and 68 are subsequently supplied via leads 70 and 72 to a microcomputer 74 which contains logic hardware and/or software capable of implementing Equations (1), (5) and (8)-(15). The exact configuration of the microcomputer will be apparent to those skilled in the art.

Figure 5A:
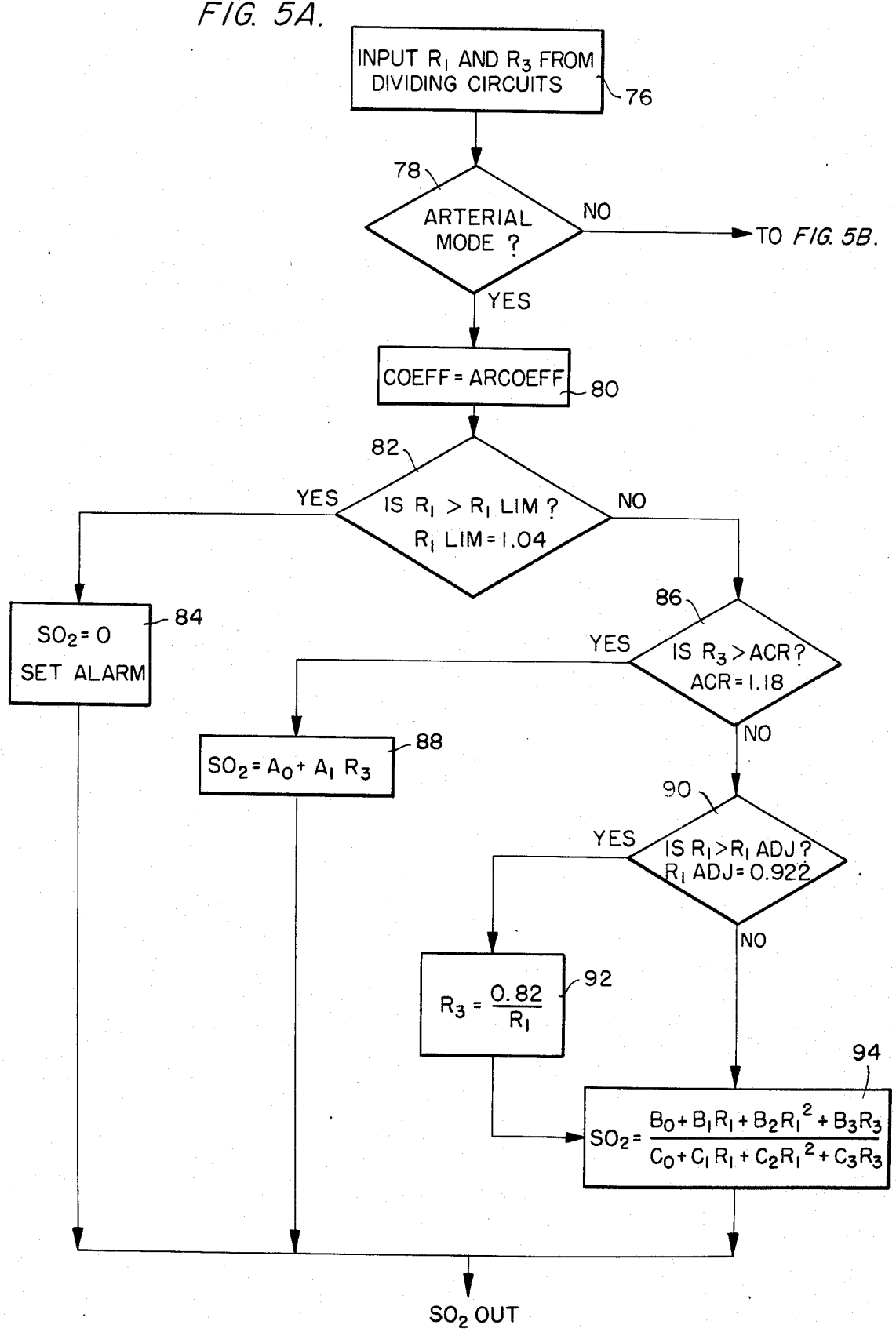
FIGS. 5A and 5B outline a flow chart for performing the various computations and comparisons necessary to obtain an accurate final indication of oxygen saturation level in accordance with the method of the present invention.
Figure 5B:
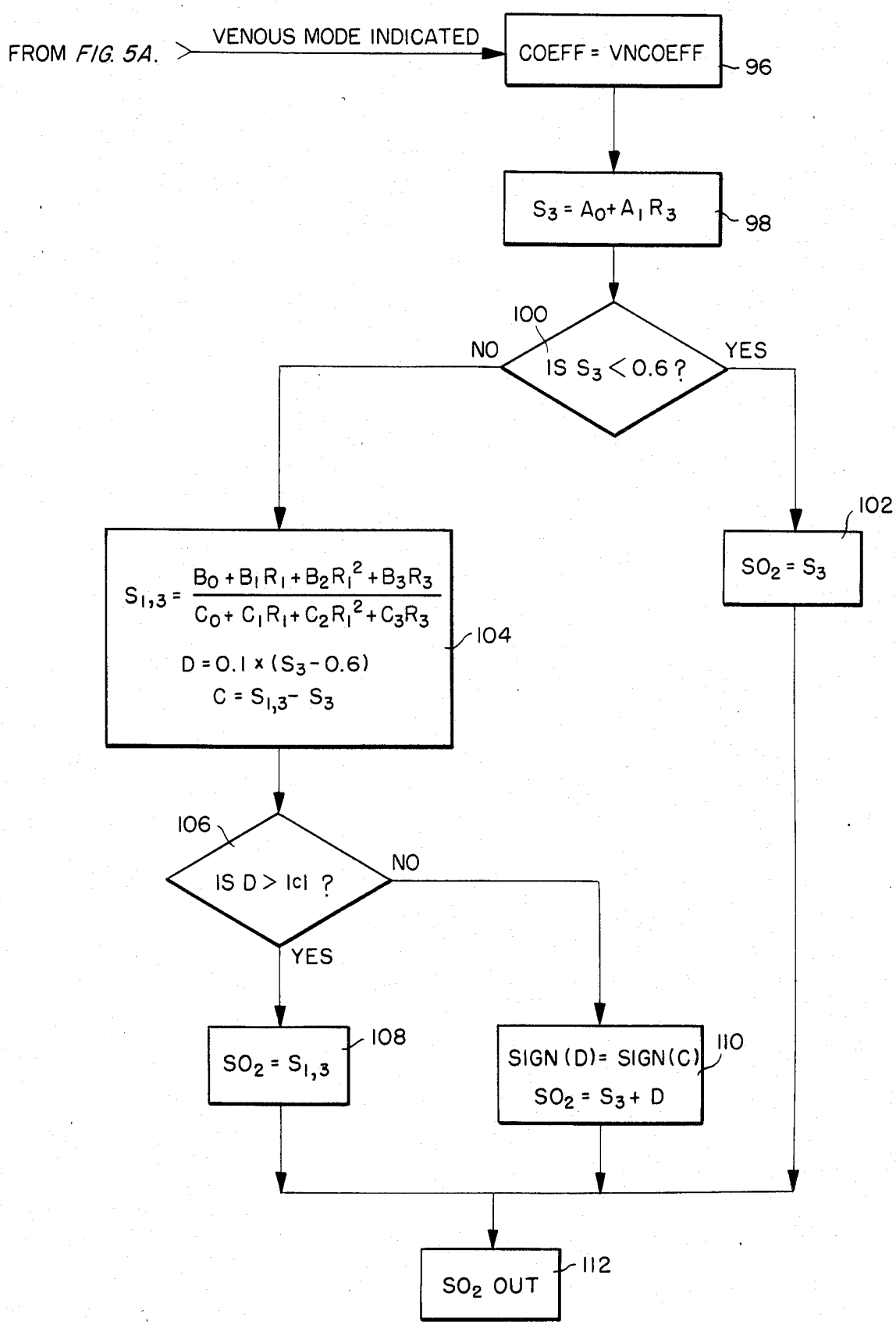

A flow chart outlining the steps taken by microcomputer 74 in performing the various calculations and comparisons of Equations (8)-(15) may be seen in FIGS. 5A and 5B. The $R_1$ and $R_3$ values from dividing circuits 66 and 68 of FIG. 4 are input to the microcomputer as indicated at program block 76 in FIG. 5A. A decision is then made at program block 78 as to whether the oximeter is operating in an arterial mode or a venous mode. This latter step is necessary because experiments have demonstrated that the empirically derived weighting coefficients of Equations (1) and (5) change slightly depending upon the location of the blood under test. The actual decision at program block 78 is based upon a signal or flag set in response to the position of a toggle switch or the like (not shown) manipulated by the oximeter operator. When the arterial mode is signalled, the $A_0$, $A_1$, $B_0$-$B_3$ and $C_0$-$C_3$ coefficients associated with the arterial mode are brought forward at program block 80. A second determination, using the value of $R_1$ derived from the detected intensities of back-scattered radiation at the $\lambda_1$ and $\lambda_2$ wavelengths, is then made at program block 82 to determine whether the oximeter is functioning properly. If $R_1$ is greater than some limit value $R_1LIM$, it is assumed that the back-scattered radiation intensities as detected by radiation detector 32 (not shown in FIG. 5A) fall outside of normal operating ranges. Such abnormal intensities may be encountered as a result of a defective detector, improper placement of the optical catheter or misalignment between the optical catheter and the detector. In any event, the oxygen saturation level reading $SO_2$ is set to zero at program block 84 and an alarm is sounded to warn the oximeter operator of the improper intensity readings.

Figure 1:
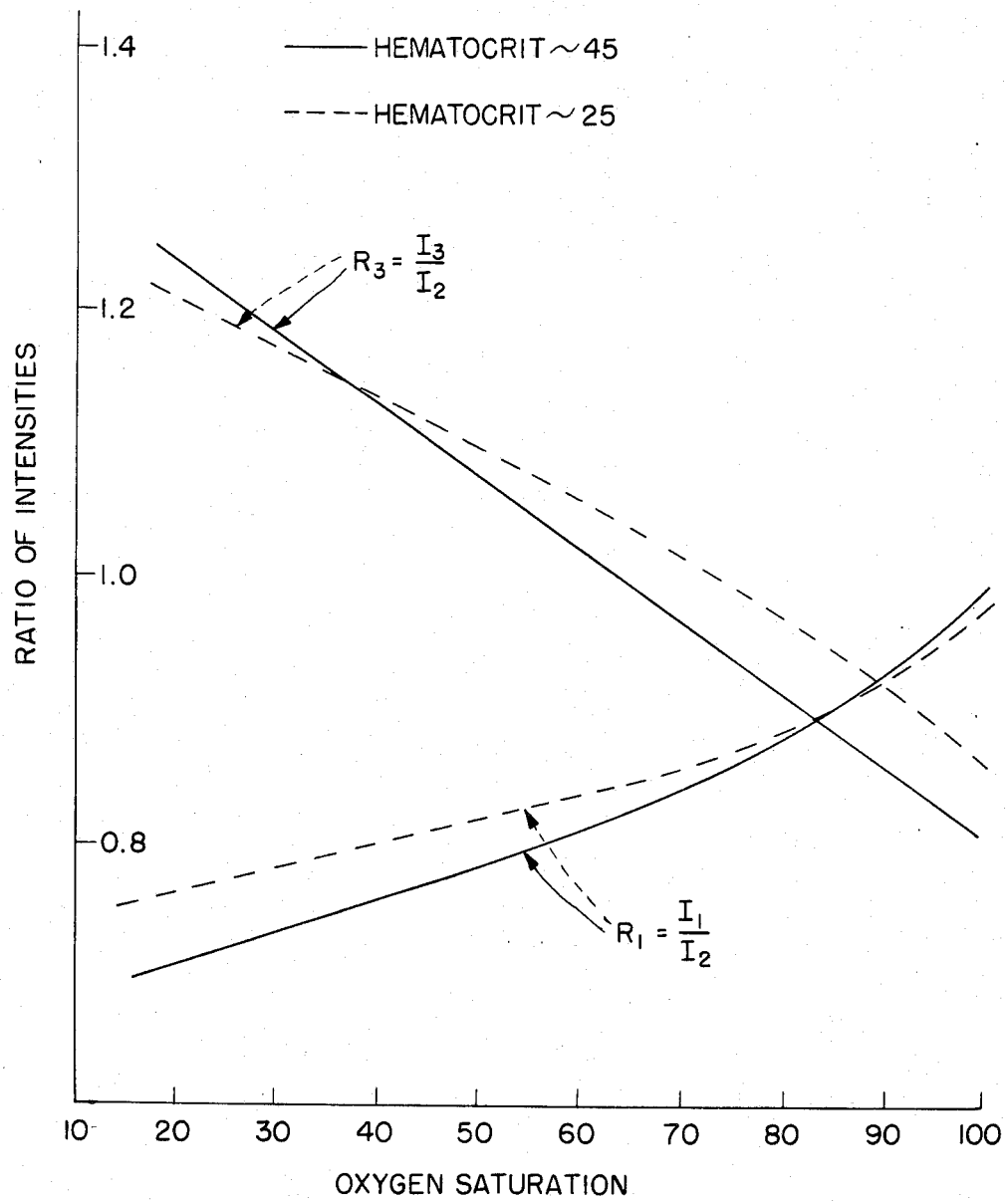
FIG. 1 graphically depicts the variation in oxygen saturation as a function of intensity ratio for two distinct values of a representative blood parameter.
Figure 2:
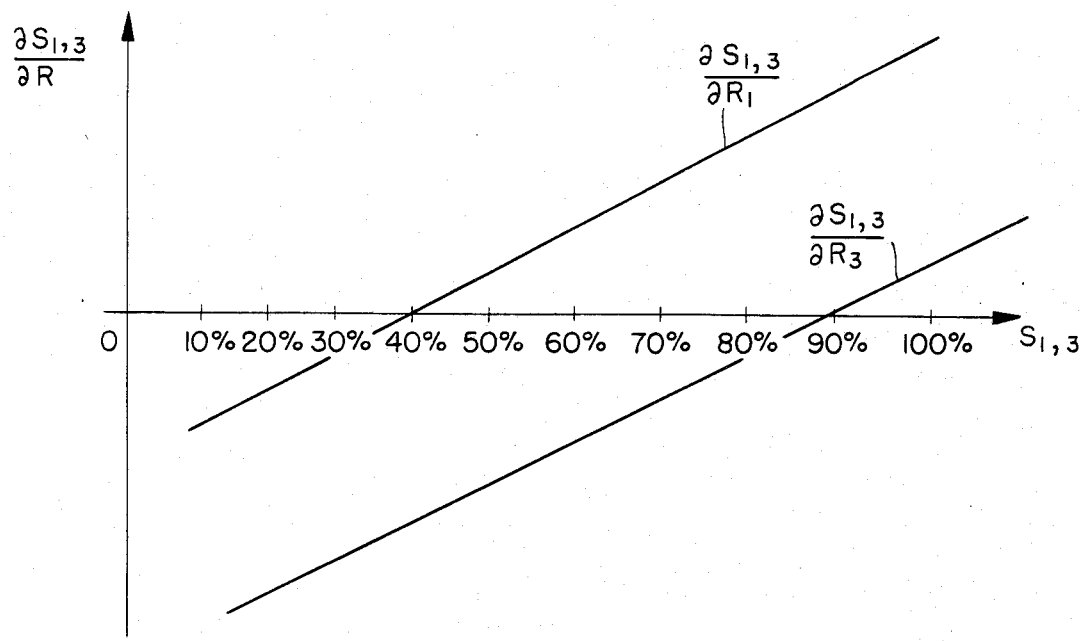
FIG. 2 graphically depicts the rate of change of Equation (5) as a function of $R_1$ with $R_3$ held constant and as a function of $R_3$ with $R_1$ held constant.

If $R_1$ is within the predetermined limits established by $R_1LIM$, $R_3$ is instead queried at program block 86 to obtain a rough indication of the magnitude of the oxygen saturation level likely to be encountered. In particular, $R_3$ is compared at program block 86 to an ACR value of approximately 1.18. As can be seen in FIG. 1, this ACR value corresponds to an oxygen saturation level of approximately 40%. If $R_3$ is greater than 1.18, the oxygen saturation level is most likely below 40% and the final oxygen saturation level reading $SO_2$ is computed using Equation (1) as indicated at program block 88. If $R_3$ is equal to or less than 1.18, the oxygen saturation level is most likely greater than 40% and Equation (5) is used to compute the final $SO_2$ or oxygen saturation level reading. First, however, the magnitude of $R_1$ is compared to an $R_1ADJ$ value of 0.922 at program block 90 in order to determine whether the value of $R_3$ should be adjusted. The determination at program block 90 is carried out because the variation in $R_3$ caused by unmeasured blood parameters at oxygen saturation levels associated with $R_1$ values above 0.922 is sufficient to render the value of $R_3$ otherwise unreliable, as may also be seen in FIG. 1. Greater accuracy in the ultimate oxygen saturation level calculation can be assured when $R_1$ is greater than 0.922 by discarding the value of $R_3$ obtained from dividing circuit 68 in favor of an empirical approximation of $R_3$. The empirically approximated value of $R_3$ is specifically derived as a function of $R_1$, as indicated at program block 92, and is ultimately employed in Equation (5) along with the value of $R_1$ obtained from dividing circuit 66 to yield the final $SO_2$ calculation as indicated at program block 94. In contrast, microcomputer 74 bypasses program block 92 when $R_1$ is less than 0.922, moving directly to program block 94 where the original values of $R_1$ and $R_3$ obtained from dividing circuits 66 and 68 are employed in Equation (5) to obtain the final $SO_2$ calculation.

FIG. 5B illustrates the routine followed by microcomputer 74 for computing oxygen saturation levels in venous blood. When the venous mode of oximeter operation is signalled at program block 78, the $A_0$, $A_1$, $B_0$-$B_3$ and $C_0$-$C_3$ coefficients are all set to values consistent with empirical data obtained during venous mode experiments, as indicated at program block 96. $S_3$ is next calculated at program block 98 using Equation (1). At program block 100, the value of $S_3$ is compared with a cut-off point of 0.6 corresponding to an oxygen saturation level of 60%. If $S_3$ is less than 0.6, the value of $S_3$ is adopted as the final oxygen saturation level reading $SO_2$ as indicated at program block 102. If the value of $S_3$ is equal to or greater than 0.6, $S_{1,3}$ is calculated using Equation (5), the deviation value D is determined in accordance with Equation (8) and the difference between $S_{1,3}$ and $S_3$ is derived in the form of a value C, all as indicated at program block 104. The value of D is compared to the absolute value of C at program block 106 to ascertain whether $S_{1,3}$ falls outside the "error envelope" defined by $S_3 \pm D$. If the absolute value of C is less than D, the value of $S_{1,3}$ differs from the value of $S_3$ by less than the tolerable deviation and the value of $S_{1,3}$ is retained as the final oxygen saturation reading $SO_2$, as indicated at program block 108. If the absolute value of C does exceed D, $S_{1,3}$ differs from the value of $S_3$ by more than the tolerable deviation and the final reading of oxygen saturation level $SO_2$ is determined at program block 110 using the limits established by the $S_3 \pm D$ curves. The actual limit calculations are performed by transferring the algebraic sign of C to D and thereafter algebraically combining $S_3$ with D. Where $S_{1,3}$ is greater than $S_3$, the algebraic sign of C will be positive and $SO_2$ will equal $S_3 + D$. Where $S_{1,3}$ is less than $S_3$, the algebraic sign of C will be negative and the value of $SO_2$ will equal $S_3 - D$. The final $SO_2$ reading can be output from microcomputer 74 at program block 112 for purposes of display and/or control.

The present invention has been set forth in the form of one preferred embodiment. It is nevertheless understood that modifications to the disclosed oximeter apparatus as well as variations in the disclosed method for computing oxygen saturation levels, particularly variations involving rearrangement of software routines or substitutions of similar equations such as those disclosed in Shaw, et al., U.S. Pat. No. 4,114,604 for implementing the oxygen saturation calculations, may be made by those skilled in the art without departing from the spirit and scope of the present invention. Moreover, such modifications and variations are considered to be within the purview of the appended claims.

What is claimed is:

1. Apparatus for determining the oxygen saturation level of blood under test, said apparatus comprising:
   generating and detection means for supplying radiation at three wavelengths to the blood under test and for detecting the intensity of back-scattered radiation emanating from the blood under test at each of said three wavelengths in response to the radiation so supplied, said generating and detection means including a first circuit means for generating intensity signals respectively representative of the intensity of said back-scattered radiation; and
   signal processing means for computing the oxygen saturation level of the blood under test, said signal processing means including a second circuit means connected to receive said intensity signals respectively representative of the intensity of said back-scattered radiation for deriving first and second ratio signals, said signal processing means also including means connected to receive said first and second ratio signals for calculating the oxygen saturation level as a function of only said first ratio signal when said oxygen saturation level is below a predetermined value and for calculating the oxygen saturation level as a function of both said first and second ratio signals when the oxygen saturation level is above said predetermined value.

2. Apparatus as set forth in claim 1, wherein said generating and detection means further includes an optical catheter structure having a single transmitting optic fiber which conducts said radiation at each of said three wavelengths to the blood under test and a single optical fiber for returning said back-scattered radiation from the blood under test to said first circuit means.

3. A method for determining the oxygen saturation level of blood under test, said method comprising the steps of:
   supplying radiation at first, second and third wavelengths to the blood under test;
   detecting the intensity of radiation back-scattered at each of said three wavelengths from the blood under test in response to the radiation so supplied;
   generating signals respectively representing the intensity of back-scattered radiation at each of said wavelengths;
   dividing said signals into one another to derive first and second ratios;
   calculating the oxygen saturation level of the blood under test as a function of only one of said ratios when the oxygen saturation level is below a predetermined value; and
   calculating the oxygen saturation level as a function of both of said ratios when the oxygen saturation level is above said predetermined value.

4. A method as set forth in claim 3, wherein said step of supplying radiation at first, second and third wavelengths to the blood under test includes the further step of transmitting said radiation to the blood under test via a single optic fiber and said step of detecting the intensity of radiation back-scattered at each of said three wavelengths from the blood under test includes the further step of collecting back-scattered radiation via a single optic fiber.

5. Apparatus for determining the oxygen saturation level of blood under test, said apparatus comprising
   means for supplying radiation at a plurality of wavelengths to the blood under test and for detecting the intensity of back-scattered radiation emanating from the blood under test at each of said wavelengths in response to the radiation so supplied,
   means for generating intensity signals representative of the intensity of said back-scattered radiation at each of said wavelengths, and
   means for computing the oxygen saturation level of the blood under test, said computing means including means connected to receive said intensity signals and generate a first ratio signal from a pair of said intensity signals and a second ratio signal from a different pair of said intensity signals, said computing means also including means connected to receive said first and second ratio signals for calculating the oxygen saturation level as a function of only said first ratio signal when said oxygen saturation level is below a predetermined value and for calculating the oxygen saturation level as a function of said second ratio signal when the oxygen saturation level is above a predetermined value.

6. Apparatus as set forth in claim 5 wherein said predetermined value for determining when only said first ratio signal is used is the same as the predetermined value used for determining when said second ratio signal is used.

7. Apparatus as set forth in claim 5 wherein said oxygen saturation value is calculated as a function of both said first and second ratio signals when the oxygen saturation level is above said predetermined value.

* * * * *